United States Patent [19]

Fukuchi

[11] Patent Number: 4,866,263
[45] Date of Patent: Sep. 12, 1989

[54] APPARATUS FOR INSPECTING SIDEWALL OF BOTTLE

[75] Inventor: Hiroyuki Fukuchi, Tokyo, Japan

[73] Assignee: Kirin Beer Kabushiki Kaisha, Tokyo, Japan

[21] Appl. No.: 112,246

[22] Filed: Oct. 21, 1987

[30] Foreign Application Priority Data

Jun. 4, 1987 [JP] Japan .................................. 62-140597

[51] Int. Cl.⁴ ............................................ G01N 21/90
[52] U.S. Cl. ................................ 250/223 B; 356/428; 356/240
[58] Field of Search .................... 356/428, 240, 307; 250/223 B

[56] References Cited

U.S. PATENT DOCUMENTS 3,411,009 11/1968 Ford et al. ...................... 356/428 X
4,029,416 6/1977 Hawes ............................. 356/307 X
4,492,476 1/1985 Miyazawa ........................... 356/428

FOREIGN PATENT DOCUMENTS 60-220850 11/1985 Japan .................................... 356/428

Primary Examiner—Vincent P. McGraw
Attorney, Agent, or Firm—Ladas & Parry

[57] ABSTRACT

An apparatus for inspecting the sidewall of a bottle, comprises an illuminating unit for applying light to the sidewall of a bottle under rotating; a photoelectric conversion unit for photoelectrically converting a light transmitted image of the sidewall applied with light by the illuminating unit into electric signals; a defect detecting unit for detecting a defect point within the light transmitted image which has been photoelectrically converted by the photoelectric conversion unit, based on the brightness of at least two points on an inspection scan line; and a judge unit for judging if the inspection scan line is a defective scan line based on the defect point detected by the defect detecting unit, judging if there is a defect on the sidewall of a bottle based on the state of continuation of defective scan lines.

The apparatus for inspecting the sidewall of a bottle of this invention detects a defective point from the light transmitted image of the sidewall of a rotating bottle, and detects if there is a defect based on the state of continuation of defective scan lines detected by the defective point.

7 Claims, 6 Drawing Sheets (a)

(b)

(a)

(b)

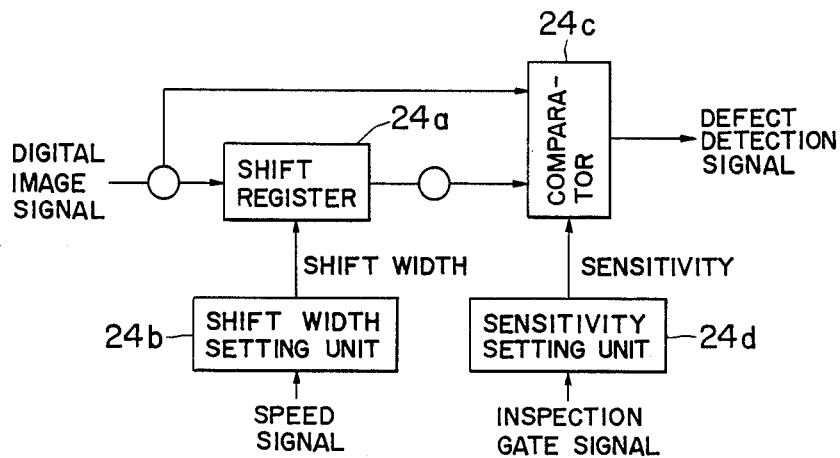
F I G. 6
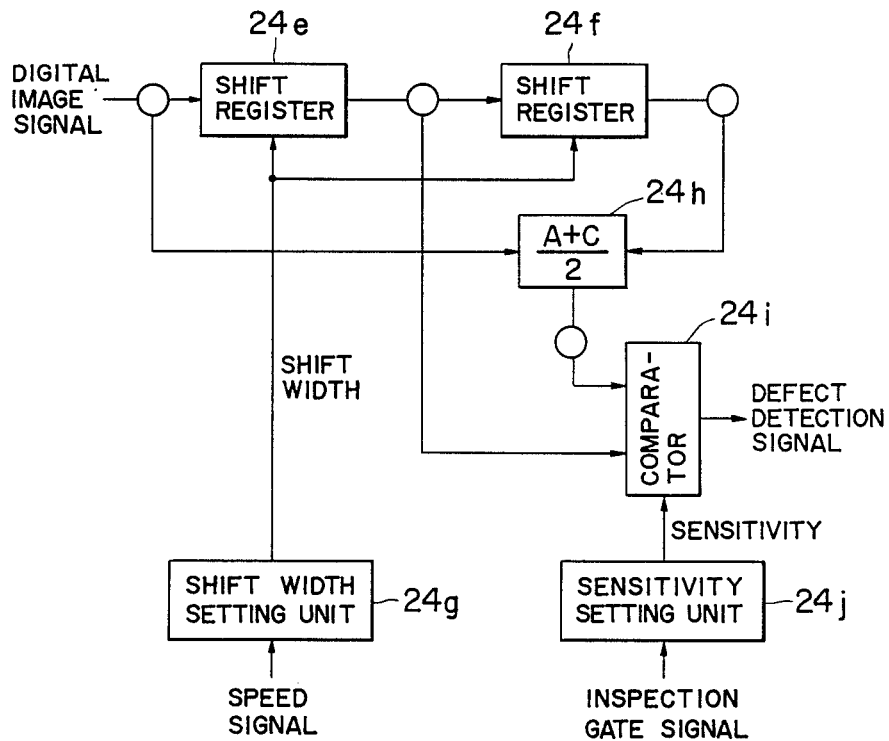
F I G. 7

APPARATUS FOR INSPECTING SIDEWALL OF BOTTLE

BACKGROUND OF THE INVENTION

The present invention relates to an apparatus for inspecting the sidewall of a bottle under rotating.

Glass bottles used for filling with liquor, refreshing drink, food or the like must be inspected as to whether there is any defect irrespective of whether they are new ones just manufactured by a bottle marker or old ones recirculated. Portions of a bottle to be inspected include its body or sidewall, bottom, top of mouth and threaded bottle neck. Of defects on the bottle sidewall, defects such as foreign matters or stains may result in a potential problem of food sanitation, and defects such as cracks or voids may result in breakage of the bottle. Thus, it is necessary to correctly detect such defects and remove defective bottles.

However, the sidewall of a bottle may have unevenness of color or thickness. Thus, such unevenness sometimes becomes an obstacle in detecting an actual defect or may be detected erroneously as a defect. In addition, there also arises a problem that because of such unevenness, it becomes difficult to properly set an inspection area or a sensitivity.

SUMMARY OF THE INVENTION

The present invention has been made in consideration of the above problems. It is an object of the present invention to provide an inspecting apparatus capable of detecting a defect on the sidewall of a bottle at high precision under rotating, and easily adjusting a sensitivity or the like.

The above object can be achieved by an apparatus for inspecting the sidewall of a bottle, which comprises illuminating means for applying light to the sidewall of a bottle while it is rotated; photoelectric conversion means for photoelectrically converting a light transmitted image of the sidewall applied with light by illuminating means into electric signals; defect detecting means for detecting a defect point within the light transmitted image which has been photoelectrically converted by photoelectric conversion means, based on the brightness of at least two points on an inspection scan line; and judge means for judging if the inspection scan line is a defective scan line based on the defect point detected by defect detecting means, and judging if there is a defect on the sidewall of a bottle based on the state of continuation of defective scan lines.

BRIEF DESCRIPTION OF THE INVENTION

FIG. 6 is a block diagram of a particular defect detection circuit practicing the defect detection method shown in FIG. 4;

FIG. 7 is a block diagram of a particular defect detection circuit practicing the defect detection method shown in FIG. 5;

DETAILED DESCRIPTION OF THE INVENTION

Figure 1:
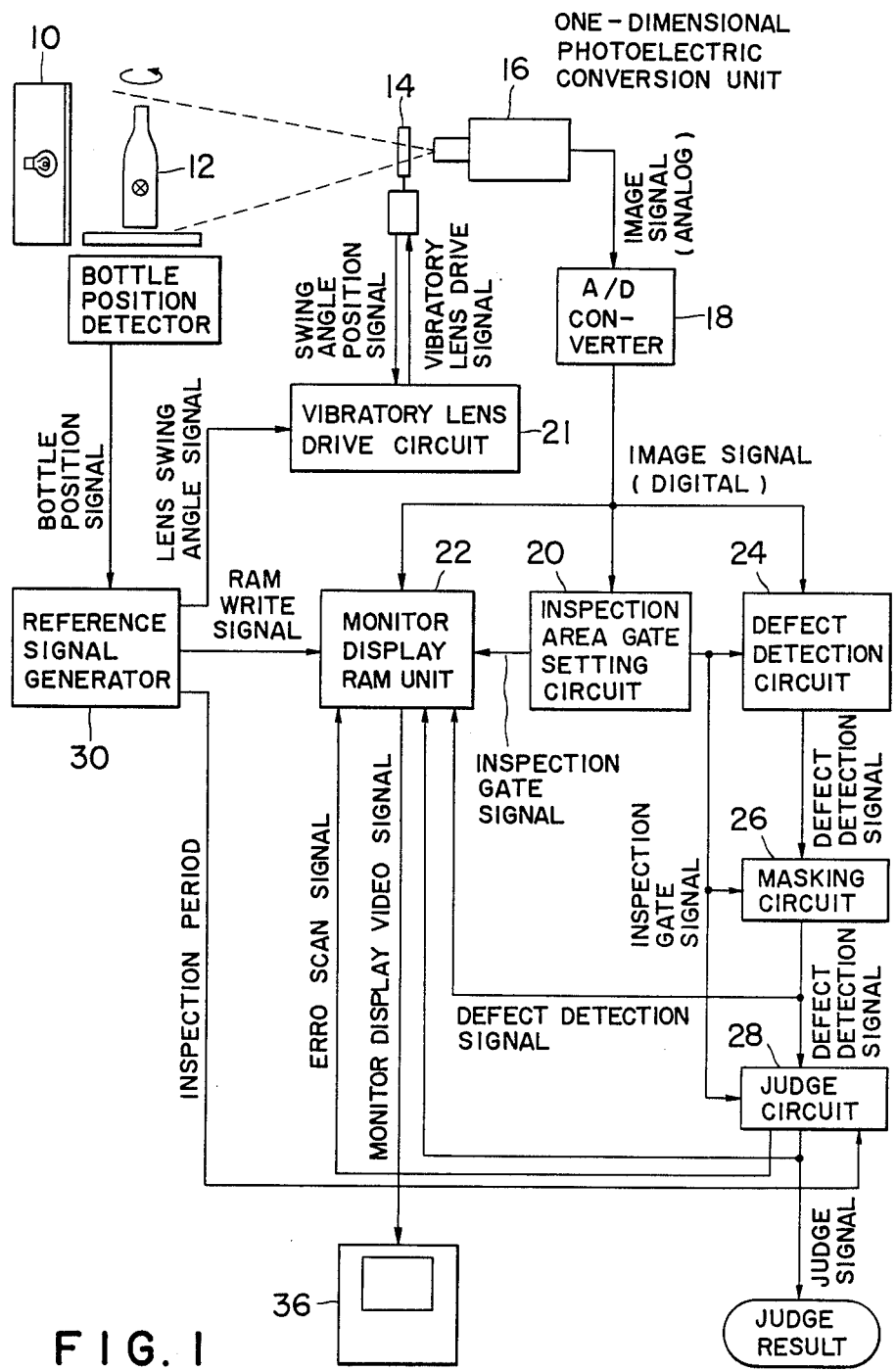
FIG. 1 is a block diagram showing an embodiment of the apparatus for inspecting a bottle sidewall according to the present invention.
Figure 2:
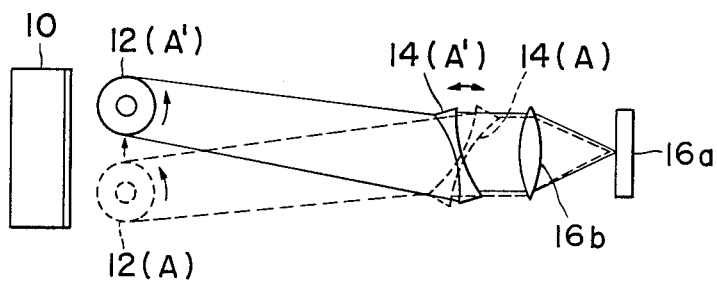
FIG. 2 shows an optical detection system of the apparatus for inspecting a bottle sidewall.

An embodiment of the apparatus for inspecting a bottle sidewall according to the present invention is shown in FIG. 1. In this embodiment, bottles 12 to be inspected are conveyed one after another while being rotated. The bottle 12 is applied with uniform diffusion light by means of a diffusion light source 10 having a radiation surface capable of radiating uniform diffusion light. A light transmitted image of the sidewall of the bottle 12 is incident to a one-dimensiomal photoelectric conversion unit 16 via a vibratory lens 14. The one-dimensional photoelectric conversion unit 16 is constructed of a light receiving portion such as a linear CCD for converting the light transmitted image into analog electric signals, and an optical system for focussing the light transmitted image onto the light receiving portion. The vibratory lens 14 is driven by a vibratory lens drive circuit 21. The vibratory lens 14 is caused to move in synchronism with the motion of the bottle 12 so as to focus the light transmitted image onto the light receiving portion of the one-dimensional photoelectric conversion unit 16. Specifically, as shown in FIG. 2, if the light receiving portion of the one-dimensional photoelectric conversion unit 16 is a linear CCD 16a and the optical system uses a convex lens 16b, then a concave lens is used as the vibratory lens and it is caused to swing or vibrate. Namely, as the bottle 12 moves from position A to position A', the concave lens 14 is rotated from position A to position A'. Therefore, the center of the light transmitted image of the bottle 12 is always focussed at a regular position on the linear CCD 16a. Since the bottle 12 is rotated once while it moves from position A to position A', the whole circumferential image of the bottle is inputted to the linear CCD 16a.

An A/D converter 18 converts an analog image signal from the one-dimensional photoelectric conversion unit 16 into a digital image signal having a predetermined number of bits. The digital image signal is supplied to an inspection area gate setting circuit 20, a monitor display RAM unit and a defect detection circuit 24.

Figure 3:
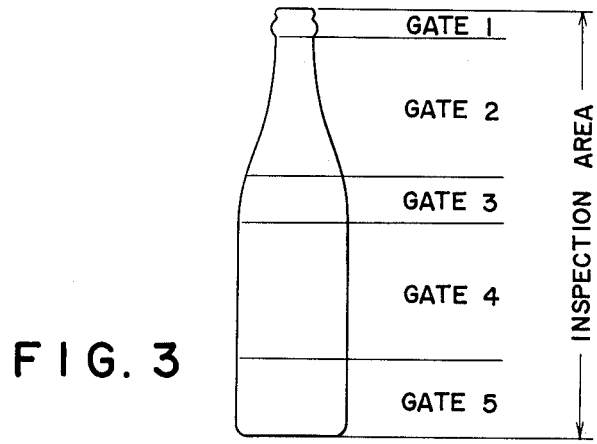
FIG. 3 shows an example of an inspection area and inspecting gates used by the apparatus for inspecting a bottle sidewall.

The inspection area gate setting circuit 20 is a circuit for determining inspection areas of the light transmitted image as shown in FIG. 3 in the vertical direction of the bottle. A defect is detected from each inspection area by a defect detection circuit described later. The overall inspection area is defined by the top and bottom of the bottle 12. The inspection area is then divided into a plurality of inspection gates in accordance with the shape of the bottle 12. In FIG. 3, the entirety of the bottle is used as the inspection area which is divided into five inspection gates 1, 2, 3, 4 and 5. The inspection area gate setting circuit 20 outputs an inspection gate signal indicative of within which inspection gate in the inspection area a current scan position of the linear CCD 16a falls, to the monitor display RAM unit 22, the defect detection circuit 24, the masking circuit 26 and a judge circuit 28.

The defect detection circuit 24 compares the brightness at a plurality of points spaced apart from each other in the vertical and horizontal directions, based on a digital image signal from the A/D converter 18.

Figure 4:
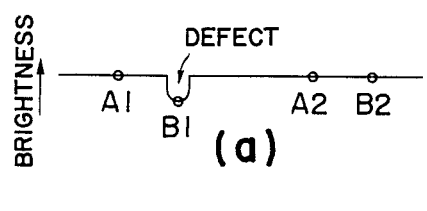
FIG. 4 shows a particular example of how a defect is detected by the apparatus for inspecting a bottle sidewall.
Figure 4:
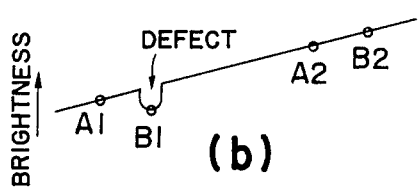
Figure 5:
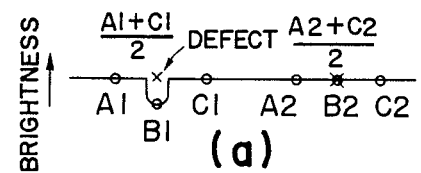
FIG. 5 shows another particular example of a defect detection method.
Figure 5:
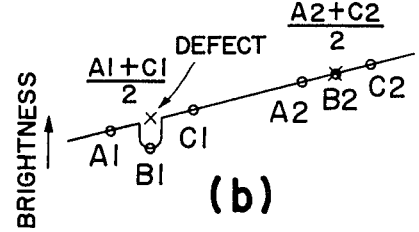

Of a defect detection method of comparing the brightness at a plurality of points, there are a two-point defect detection method of detecting a defect through comparison of the brightness at two points, and a three-point defect detection method of detecting a defect through comparison of the brightness at three points. FIG. 4 illustrates the two-point defect detection method, and FIG. 5 illustrates the three-point defect detection method.

According to the two-point defect detection method, it is considered that there is a defect if the following formula stands, wherein QA and QB represent the brightness at two points A and B to be compared and calculated, respectively.

$$|QA - QB| \geq \text{(constant A)}$$

In case of FIG. 4, it is considered that there is a defect if the following formula stands, wherein QA1, QB1, QA2 and QB2 represent the brightness at points A1, B1, A2 and B2 to be compared and calculated, respectively.

$$|QA1 - QB1| \geq A$$

$$|QA2 - QB2| \geq A$$

The constant A is determined beforehand based on the types of bottles and the like. If the light transmitted image on a scan line is uniform as shown in FIG. 4(a), the following formulas stand, and point B1 is decided as a defective point.

$$QA1 - QB1 > A$$

$$QA2 - QB2 = 0$$

The two-point defect detection method is valid on condition that the brightness on a scan line is uniform. However, as shown in FIG. 4(b) if the brightness of the light transmitted image on a scan line is not uniform, the above two formulas become $$|QA1 - QB1| < A$$

$$|QA2 - QB2| < A$$

so that a defect at point B1 cannot be detected.

Even in such a case, the three-point defect detection method detects correctly such as defective point. According to the three-point defect detection method, a defect is detected by the following formula, wherein QA, QB and QC represent the brightness at three points A, B and C to be compared and calculated, respectively.

$$|QB - [(QA + QC)/2]| \geq \text{(constant B)}$$

The constant B is determined beforehand based on the types of bottles and the like. In case of FIG. 5, the following formulas are used for the detection of a defect, wherein QA1, QB1, QC1, QA2, QB2 and QC2, represent the brightness at points A1, B1, C1, A2, B2 and C2 on a scan line of the linear CCD 16a to be compared and calculated, respectively.

$$|QB1 - [(QA1 + QC1)/2]| \geq B$$

$$|QB2 - [(QA2 + QC2)/2]| \geq B$$

Since the brightness to be compared with that at intermediate points B1 and B2 is the brightness of an arithmetic means value of opposite points A1 and C1, and A2 and C2, respectively, a defective point B1 is detected correctly both in case of FIG. 5(a) with uniform brightness and in case of FIG. 5(b) without uniform brightness.

FIG. 6 is a particular block diagram showing an example of the defect detection circuit 24 using the two-point defect detection method. The interval between two points is determined by a shift width of a shift register 24a into which a digital image signal is sequentially inputted. The shift width is set by a shift width setting unit 24b. A comparator 24c compares a current digital image signal and a previous one delayed by a shift width and outputted from the shift register 24a, and judges if the resultant difference is larger than a sensitivity (i.e., constant A) set by a sensitivity setting unit 24d to accordingly output a defect detection signal. The constant A differs depending upon an inspection gate so that the sensitivity setting unit 24d supplies an appropriate constant A to the comparator, in accordance with an inputted inspection gate signal.

FIG. 7 is a particular block diagram showing an example of the defect detection circuit 24 using the three-point defect detection method. The interval among three points is decided by a shift width of shift registers 24e and 24f into which digital image signals are sequentially inputted. The shift width of the shift registers 24a and 24f are set by a shift width setting unit 24g. In this embodiment, the shift width of the two shift registers 24e and 24f are set at a same shift width. An operation circuit 24h calculates an arithmetic mean value of a current digital image signal and a digital image signal outputted from the shift register 24f. A comparator 24i compares the means brightness calculated by the operation circuit 24h with a digital image signal from the shift register 24e, and judges if the resultant difference is larger than a sensitivity (i.e., constant B) set by a sensitivity setting unit 24j to accordingly output a defect detection signal. The constant B differs depending upon an inspection gate so that the sensitivity setting unit 24j supplies an appropriate constant B to the comparator 24i, in accordance with an inputted inspection gate signal.

The defect detection circuits shown in FIGS. 6 and 7 compare the brightness at two or three points on a scan line (i.e., in the vertical direction with respect to the bottle 12) of the linear CCD 16a. If the brightness at two or three points in the horizontal direction with respect to the bottle 12 is to be compared, digital image signals for several scan lines necessary for such comparison are stored in a memory (not shown). Then digital image signals are read from the memory sequentially from the upper scan line to the lower scan line in the vertical direction, to input them to the shift register 24a or 24e. In this case, since the digital image signal inputted to the shift register 24a or 24b varies with the spinning speed of the bottle 12, a speed signal is supplied to the shift width setting unit 24b or 24g for setting a shift width. For example, by setting four different shift widths for covering the spinning speed of the bottle 12, it becomes possible to compare two or three points spaced apart from each other by substantially an equal distance, irrespective of a different spinning speed.

A defect detection signal outputted from the defect detection circuit 24 is subjected to a masking process by the masking circuit 26. If the sensitivity of the defect detection circuit 24 is made high in order not to fail to detect a small defect, a point which is not defective may erroneously be detected as a defective point. The masking process removes such an erroneous defect detection signal. An actual defective portion will generate consecutive defect detection signals depending on the dimension of a defect, whereas a portion which is not defective will generate dispersed defect detection signals. Therefore, in the masking process, an isolated defect detection signal or those consecutive signals having a smaller value than a certain setting value are considered as non-defect and removed.

The judge circuit 28 judges if a defect is present based on a defect detection signal after processed by the masking circuit 26. For example, if the number of defect detection signals counted for each scan exceeds a predetermined setting value, then the scan is considered as an error scan (defective scan line). The number of consecutive error scans is further counted, and if the count number exceeds a predetermined setting value, it is considered as a defective bottle. This judge signal is fed to a conveying system (not shown) of the bottle 12 so that the conveying system ejects out the defective bottle 12 in accordance with the judge result.

A reference signal generator 30 generates a lens swing angle signal, an inspection period signal and a RAM wire signal, based on a bottle position signal from a bottle position detector 32. The lens swing angle signal is used for vibrating the vibratory lens 14 such that an image on a center line of the bottle can be obtained always on the one-dimensional photoelectric conversion unit 16. The lens swing angle signal is outputted to a vibratory lens drive circuit 34 which causes the vibratory lens 14 to vibrate in accordance with the lens swing angle signal. The inspection period signal is used for indicating an inspection period during which the vibratory lens 14 is caused to track the movement of the bottle 12. The inspection period signal is outputted to the judge circuit 28. The RAM write signal is used for indicating a timing when a digital image signal is written in a monitor display RAM unit 22. Thus, a monitor 30 displays digital image signals of, for example, 480 scans at equal intervals during the inspection period indicated by the inspection period signal.

Figure 8:
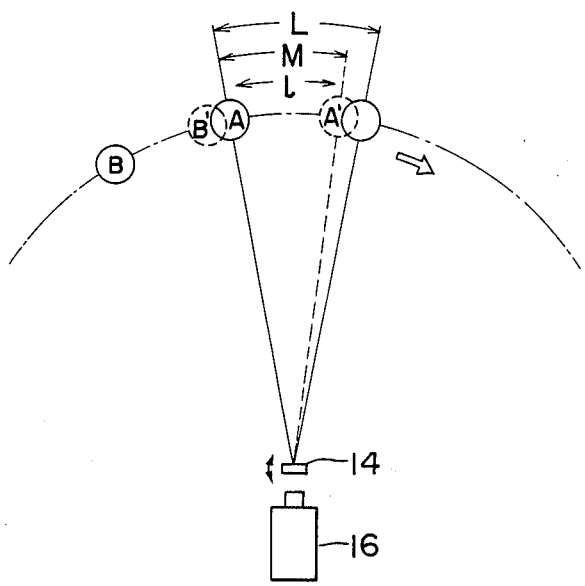
FIGS. 8 and 9 show a relationship among a position of a bottle, a lens swing angle signal, an inspection period signal, and a RAM write signal, respectively used by the apparatus for inspecting a bottle sidewall.
Figure 9:
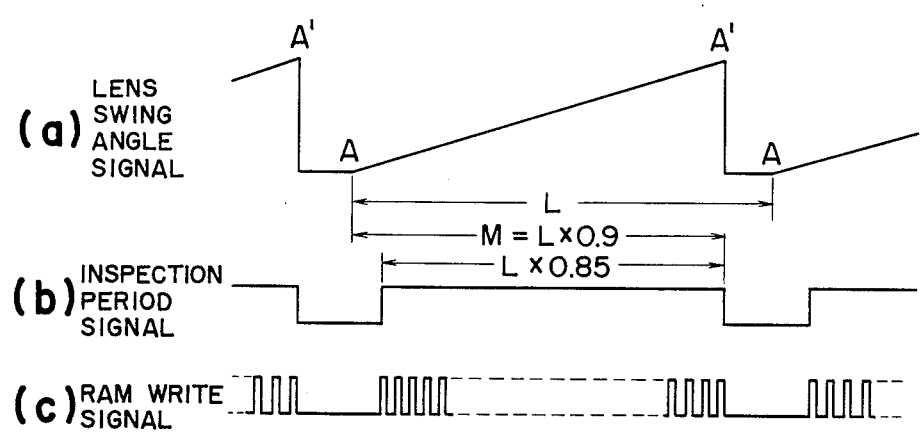

A relationship between the position of the bottle 12 and the lens swing angle signal, inspection period signal and RAM write signal is shown in FIGS. 8 and 9. In FIG. 9, L represents a pitch between bottles 12 conveyed continuously, l (=L×0.8) represents a distance of movement after the bottle 12 is rotated once, and M (=L ×0.9) represents a distance that the vibratory lens 14 tracks the bottle 12.

The lens swing angle signal changes in order for the vibratory lens 14 to track the movement of the bottle 12 while the bottle moves from point A to point A'. In case where the bottle 12 moves along a circle whose center is the position of the vibratory lens 14, the lens swing angle signal is represented by a straight line with a predetermined inclination as shown in FIG. 9(a). When the bottle 12 reaches point A', the vibratory lens 14 immediately changes to return to point A. Since the bottle 12 is still at point B' at that time, the lens swing angle signal does not change until the bottle reaches point A. When the bottle 12 reaches again point A, the lens swing angle signal changes in order for the vibratory lens 14 to track the movement of the bottle 12.

The inspection period signal indicates a period of the distance l while the bottle 12 rotates once within the distance M while the vibratory lens 14 tracks the movement of the bottle 12. In particular, for example, the inspection period signal becomes high level during the period L×0.85 (>l) as shown in FIG. 9(b).

The RAM write signal is constructed of pulse signals corresponding in number to that of scan lines for scanning the entire circumference of the bottle 12. For example, if 480 scan lines are to be used for the entire circumference of the bottle 12 and written in the monitor display RAM unit 22, a RAM write signal of 480 pulses are outputted during the high level period of the inspection period signal as shown in FIG. 9(c).

The reference signal generator 30 uses a ROM for the generation of the lens swing angle signal, inspection period signal and RAM write signal. Particularly, lens swing angle signals, inspection period signals and RAM write signals are written beforehand in the ROM at addresses for various bottle position signals. Thus, a proper lens swing angle signal, inspection period signal and RAM write signal can be obtained using a bottle position signal as an address.

The vibratory lens drive circuit 21 drives the vibratory lens 14 in accordance with a lens swing angle signal from the reference signal generator 30. The vibratory lens drive circuit 21 is feedback-controlled by a feedback signal of a swing angle position signal from the vibratory lens 14 side. If a swing angle position signal from the vibratory lens 14 side is not used, the vibratory lens drive circuit 21 is controlled in open-loop.

An inspection period signal from the reference signal generator 30 is outputted, for example, to the judge circuit 28. The judge circuit 28 makes valid only those defect detection signals inputted during the high level of the inspection period signal, to thereby judge if the bottle 12 is defective or not. The inspection period signal may also be outputted to the inspection area gate setting circuit 20, defect detection circuit 24 or masking circuit 26 to make valid only those signals inputted during the high level of the inspection period signal.

A RAM write signal from the reference signal generator 30 is outputted to the monitor display RAM unit 22. A digital image signal from the A/D converter 18 is written in the monitor display RAM circuit 22 in response to the RAM write signal. In addition to the RAM write signal, inputted to the monitor display RAM unit 22 are a defect detection signal from the masking circuit 26, an error scan signal and a judge signal from the judge circuit 28 and an inspection gate signal from the inspection area gate setting circuit 20. A defective point and an error scan are written in the monitor display RAM circuit 22 in accordance with a defect detection signal and an error scan signal. An inspection gate is displayed on the monitor 36 in accordance with an inspection gate signal.

The monitor display RAM circuit 22 has two frame memories which are alternatively used to store a digital image signal of the bottle 12 now under inspection and a preceding digital image signal of the bottle 12. In a normal state, digital image signals of the bottle 12 are sequentially displayed on the monitor 36. However, if a judge signal from the judge circuit 28 indicates a defective bottle, then the contents of the frame memory in which digital image signals of the defective bottle have been stored are displayed on the monitor 36 to inspect the detail of defective condition.

As described so far, according to the above embodiment, it is possible to detect a defect of the sidewall of bottles continuously conveyed while rotating and inspect the detail of defective condition. Further, although a linear sensor is used in this embodiment, a two-dimensional image of the entirety of a bottle can be displayed on a monitor television. Thus, the embodiment can be used as an adjustment apparatus for adjusting the optical system while viewing the display on the monitor television.

The present invention is not limited to the above embodiment only, but various modifications are possible which are described hereinafter.

Figure 10:
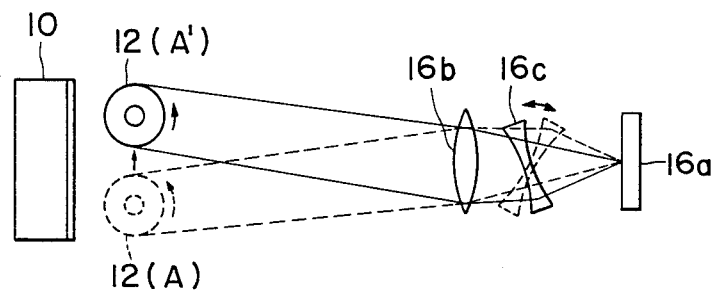
FIG. 10 shows another example of a particular optical detection system employing a vibratory lens in the apparatus for inspecting a bottle sidewall.
Figure 11:
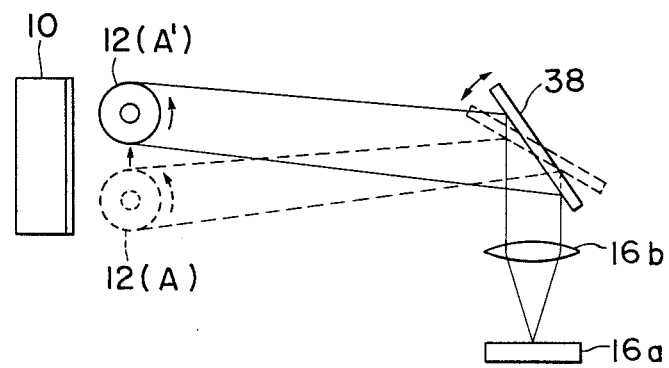
FIG. 11 shows an example of a particular optical detection system employing a vibratory mirror in the apparatus for inspecting a bottle sidewall.

In the above embodiment, the vibratory lens 14 is mounted between the optical system 16b of the one-dimensional photoelectric conversion unit 16 and the bottle 12, as shown in FIG. 2. However, as shown in FIG. 10 a vibratory lens 16c may be mounted as serving a part of the optical system of the one-dimensional photoelectric conversion unit 16, to cause the vibratory lens 16c to move by tracking the movement of the bottle 12. Further, instead of the vibratory lens, a vibratory mirror 38 may be used as shown in FIG. 11 to cause it to move by tracking the movement of the bottle 12.

Figure 12:
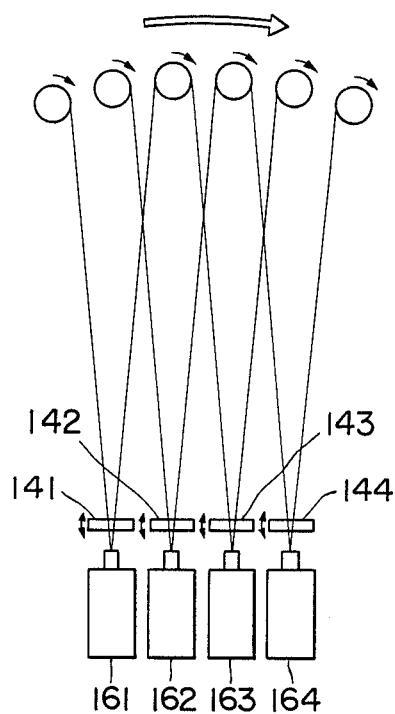
FIG. 12 shows an example of a particular optical detection system of the apparatus for inspecting a bottle sidewall, wherein the bottle is spun at a fixed position.

In case where a vibratory lens is used, the optical detection system constructed of a vibratory lens and a one-dimensional photoelectric conversion unit is aligned on a straight line so that a plurality of optical detection systems can be disposed laterally. Therefore, in case where bottles 12 are conveyed continuously at so high a speed that a defect cannot be detected using a single optical system, bottles 12 conveyed at high speed can be inspected using, for example, four optical detection systems disposed side by side and constructed of vibratory lenses 141, 142, 143 and 144 and one-dimensional photoelectric conversion units 161, 162, 163 and 164 as shown in FIG. 12.

Figure 13:
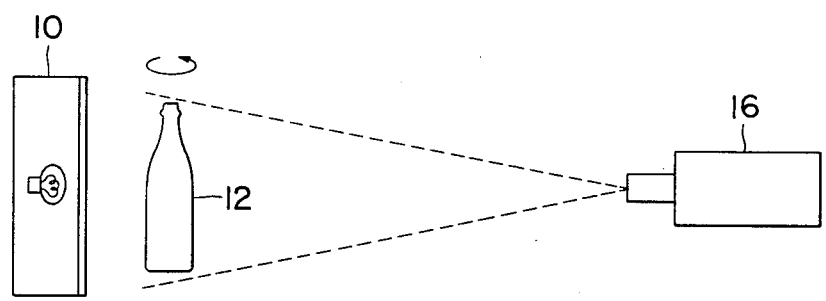
FIG. 13 shows a plurality of optical detection systems mounted on the apparatus for inspecting a bottle sidewall.

A bottle 12 conveyed continuously while rotating has been inspected in the above embodiment. However, as shown in FIG. 13 a bottle 12 rotating at a fixed position may be inspected, wherein without using a vibratory lens or mirror, a fixed one-dimensional photoelectric conversion unit 16 may be used to obtain a light transmitted image of a whole circumference of a bottle 12.

Furthermore, a one-dimensional photoelectric conversion unit has been used for detection of a light transmitted image of a bottle 12. However, a two-dimensional photoelectric conversion unit such as an area CCD may be used.

The defect detection method is not intended to be limited to those shown in the above embodiment, but various modifications are possible. For example, it may be considered as defective if any one of the following formulas stands, wherein the brightness at two points is QA and QB.

$$QA/QB \geq (constant\ C)$$

$$QA/QB \leq 1/(constant\ C)$$

Also, it may be considered as defective if any one of the following formulas stands, wherein the brightness at three points is QA, QB and QC.

$$QB/[(QA+QC)/2] \geq (constant\ D)$$

$$QB/[(QA+QC)/2] \leq 1/(constant\ D)$$

where constant C and D are a numeral larger than 1.

As seen from the foregoing description of the invention, a defect on the sidewall of a bottle while rotating can be detected precisely by properly setting an inspection area, properly adjusting a sensitivity and the like.

What is claimed is:

1. An apparatus for inspecting the side wall of a bottle, comprising:
   illuminating means for applying light to the side wall of the bottle as the bottle is rotated;
   photoelectric conversion means for photoelectrically converting a light transmitted image of the side wall to which the light is applied by said illuminating means into electric signals;
   defect detection means for detecting a defect point within the light transmitted image which has been photoelectrically converted by said photoelectric conversion means, wherein said defect detecting means detects a defective point on the basis of brightness at three adjacent points on a defective scan line by comparing the means value of the brightness at opposite two points with the brightness at an intermediate point therebetween, said defect detecting means comprising a first and a second shift registers for deciding an interval among said three adjacent points on the basis of a preset shift width, an operation circuit for calculating said mean value of the brightness on the basis of an input image signal from said photoelectric conversion means and an output signal from said second shift register, and a comparator for comparing said mean value of the brightness output from said operation circuit with an output signal from said first shift register and outputting a defect detection signal; and
   judgment means for judging if said inspection scan line is a defective scan line on the basis of the defect point detected by said defect detecting means, and judging if there is a defect on the side wall of a bottle on the basis of state of continuation of defective scan lines.

2. An apparatus for inspecting the side wall of a bottle according to claim 1, wherein said apparatus further comprising an inspection area setting means for setting a predetermined area within the light transmitted image for which said defect detecting means performs the defect detection.

3. An apparatus for inspecting a side wall of a bottle according to claim 1, wherein said apparatus further comprising an optical path change means for changing the optical path from said bottle to said photoelectric conversion means so as to sequentially focus the light transmitted image of said bottle onto said photoelectric conversion means.

4. An apparatus for inspecting a side wall of a bottle according to claim 2, wherein said apparatus further comprising an optical path change means for changing the optical path from said bottle to said photoelectric conversion means so as to sequentially focus the light transmitted image of said bottle onto said photoelectric conversion means.

5. An apparatus for inspecting a side wall of a bottle according to claim 3, wherein said optical path change means further comprising a vibratory means for causing a lens positioned in an optical path from said bottle to said photoelectric conversion means to vibrate so as to track the movement of said bottle.

6. An apparatus for inspecting a side wall of a bottle according to claim 4, wherein said optical path change means further comprising a vibratory means for causing a lens positioned in an optical path from said bottle to said photoelectric conversion means to vibrate so as to track the movement of said bottle.

7. An apparatus for inspecting a side wall of a bottle according to claim 4, wherein said optical path change means further comprising a vibratory means for causing a mirror positioned in an optical path from said bottle to said photoelectric conversion means to vibrate so as to track the movement of said bottle.

* * * * *